(12) United States Patent
Fischer et al.

(10) Patent No.: US 7,198,623 B2
(45) Date of Patent: Apr. 3, 2007

(54) FIBER-COATED DENTAL INFUSOR SYSTEMS AND METHODS OF USE

(75) Inventors: Dan E. Fischer, Sandy, UT (US); Paul Lewis, Midvale, UT (US)

(73) Assignee: Ultradent Products, Inc., South Jordan, UT (US)

( * ) Notice: Subject to any disclaimer, the term of this patent is extended or adjusted under 35 U.S.C. 154(b) by 747 days.

(21) Appl. No.: 10/340,198

(22) Filed: Jan. 10, 2003

(65) Prior Publication Data

US 2004/0138642 A1    Jul. 15, 2004

(51) Int. Cl.
    *A61M 31/00*    (2006.01)
(52) U.S. Cl. .................................................. 604/500
(58) Field of Classification Search ................ 604/310, 604/311, 2, 500; 433/80, 81, 89, 224; 401/129, 401/271; 15/162.1
    See application file for complete search history.

(56) References Cited

U.S. PATENT DOCUMENTS

| | | | |
|---|---|---|---|
| 717,594 A | 1/1903 | Miles, Jr. | |
| 767,469 A | 8/1904 | Ziegler | |
| 2,145,570 A | 1/1939 | Miettunen | 15/137 |
| 3,048,170 A | 8/1962 | Lemos | 128/172.1 |
| RE25,483 E | 11/1963 | Lemos | 128/172.1 |
| 3,359,992 A | 12/1967 | Cishek et al. | 132/85 |
| 3,417,762 A | 12/1968 | Hall | 132/84 |
| 3,499,686 A | 3/1970 | Landen et al. | 300/21 |
| 3,581,399 A | 6/1971 | Dragan | 32/60 |
| 3,900,954 A | 8/1975 | Dragan | 32/60 |
| 4,198,756 A | 4/1980 | Dragan | 222/326 |
| 4,199,270 A | 4/1980 | Tomasini | 401/183 |
| 4,211,247 A | 7/1980 | Morganroth | 132/88.7 |
| 4,222,677 A | 9/1980 | Cervantes | 401/129 |
| 4,256,409 A | 3/1981 | Manley | 401/24 |
| 4,330,280 A | 5/1982 | Dougherty et al. | 433/90 |
| 4,391,590 A | 7/1983 | Dougherty | 433/90 |
| 4,551,100 A * | 11/1985 | Fischer | 433/218 |
| 4,578,055 A | 3/1986 | Fischer | 604/2 |
| 4,619,613 A | 10/1986 | Dragan | 433/90 |

(Continued)

FOREIGN PATENT DOCUMENTS

DE    3 436 472    4/1986

(Continued)

OTHER PUBLICATIONS

Richard E. Walton, D.M.D. and Mahmoud Torabinejad, D.M.D., "*Principles and Practice of Endodontics*", Second Edition, pp. 202-205, p. 230, and title page, available on information and belief at least as early as Jan. 23, 2001.

(Continued)

*Primary Examiner*—Manuel Mendez
(74) *Attorney, Agent, or Firm*—Workman Nydegger (57) ABSTRACT

A method for controlling bleeding during dental procedures using a medicament delivery system having a medicament under pressure and a hollow cannula having a fiber coated distal delivery end through which the medicament is dispensed, includes: (i) applying under hydraulic pressure a medicament to a desired area of tissue using the medicament delivery system so as to infuse medicament into exposed capillaries; and (ii) rubbing the tissue with the medicament delivery system.

41 Claims, 3 Drawing Sheets

U.S. PATENT DOCUMENTS

| | | | |
|---|---|---|---|
| 4,672,953 A | 6/1987 | DiVito | 128/66 |
| D292,825 S | 11/1987 | Dragan | D24/16 |
| 4,718,889 A | 1/1988 | Blasius, Jr. et al. | 604/1 |
| 4,738,669 A | 4/1988 | Vlock | 604/289 |
| 4,767,398 A | 8/1988 | Blasius, Jr. | 604/1 |
| 4,808,022 A | 2/1989 | Iizuka et al. | 401/176 |
| 4,863,380 A | 9/1989 | Creed | 433/89 |
| 4,922,936 A | 5/1990 | Buzzi et al. | |
| 4,941,873 A | 7/1990 | Fischer | 604/54 |
| 4,963,046 A | 10/1990 | Eguchi | 401/160 |
| 4,963,093 A | 10/1990 | Dragan | 433/90 |
| 4,969,816 A | 11/1990 | Drumm | 433/90 |
| 4,997,371 A | 3/1991 | Fischer | |
| 5,001,803 A | 3/1991 | Discko, Jr. | 15/167.1 |
| D315,956 S | 4/1991 | Dragan | D24/14 |
| 5,052,927 A | 10/1991 | Discko, Jr. | 433/90 |
| 5,083,921 A | 1/1992 | Dragan | 433/90 |
| 5,119,803 A | 6/1992 | Fishman | 128/62 A |
| 5,122,057 A | 6/1992 | Discko, Jr. | 433/90 |
| 5,127,831 A | 7/1992 | Bab | 433/80 |
| 5,129,825 A | 7/1992 | Discko, Jr. | 433/90 |
| 5,150,495 A | 9/1992 | Discko, Jr. et al. | 15/167.1 |
| 5,154,523 A | 10/1992 | Devreeze | 401/144 |
| 5,165,890 A | 11/1992 | Discko, Jr. | 433/90 |
| 5,172,807 A | 12/1992 | Dragan et al. | 206/219 |
| 5,236,355 A | 8/1993 | Brizzolara et al. | 433/80 |
| 5,236,358 A | 8/1993 | Sieffert | 433/119 |
| 5,244,388 A | 9/1993 | Frush | 433/90 |
| 5,246,371 A | 9/1993 | Fischer | 433/217.1 |
| 5,267,859 A | 12/1993 | Discko, Jr. | 433/89 |
| 5,269,684 A | 12/1993 | Fischer | 433/90 |
| 5,286,257 A | 2/1994 | Fischer | 604/82 |
| 5,324,273 A | 6/1994 | Discko, Jr. | 604/240 |
| 5,336,088 A | 8/1994 | Discko, Jr. | 433/90 |
| 5,337,436 A | 8/1994 | Saxer | |
| 5,378,149 A | 1/1995 | Stropko | 433/80 |
| D359,119 S | 6/1995 | Dragan et al. | D24/114 |
| 5,460,523 A | 10/1995 | Schulman | 433/90 |
| 5,570,966 A | 11/1996 | Phelan | 401/183 |
| 5,630,244 A | 5/1997 | Chang | 15/167.1 |
| 5,693,360 A | 12/1997 | Stern et al. | 427/2.29 |
| 5,707,234 A | 1/1998 | Bender | 433/90 |
| 5,755,572 A | 5/1998 | Bab et al. | 433/80 |
| 5,800,367 A | 9/1998 | Saxer et al. | 601/164 |
| 5,816,804 A | 10/1998 | Fischer | 433/90 |
| 5,829,976 A | 11/1998 | Green | 433/89 |
| 5,899,693 A | 5/1999 | Himeno et al. | 433/119 |
| 5,908,257 A | 6/1999 | Martin | 401/271 |
| 5,944,519 A | 8/1999 | Griffiths | 433/80 |
| 6,012,921 A | 1/2000 | Riitano | |
| 6,049,934 A | 4/2000 | Discko | 15/106 |
| 6,059,570 A * | 5/2000 | Dragan et al. | 433/80 |
| 6,082,999 A | 7/2000 | Tcherny et al. | 433/80 |
| 6,083,002 A | 7/2000 | Martin et al. | 433/90 |
| 6,096,382 A | 8/2000 | Gueret | 427/463 |
| 6,162,202 A | 12/2000 | Sicurelli et al. | 604/272 |
| 6,179,617 B1 | 1/2001 | Ruddle | 433/224 |
| D441,074 S | 4/2001 | Mark | D24/119 |
| 6,238,120 B1 | 5/2001 | Mark | 401/265 |
| D444,229 S | 6/2001 | Mark | D24/119 |
| D447,242 S | 8/2001 | Mark | D24/176 |
| 6,286,246 B1 | 9/2001 | Rachal et al. | |
| 6,343,929 B1 | 2/2002 | Fischer | |
| 6,382,972 B1 | 5/2002 | Fischer et al. | |
| 6,431,863 B1 | 8/2002 | Sachdeva et al. | |
| 6,638,067 B2 | 10/2003 | Fischer et al. | |
| 6,932,605 B2 | 8/2005 | McLean et al. | |
| 2002/0090591 A1 | 7/2002 | Fisher | |
| 2002/0172922 A1 | 11/2002 | Mannschedel | 433/102 |

FOREIGN PATENT DOCUMENTS

| | | |
|---|---|---|
| DE | 39 37 030 | 5/1990 |
| DE | 39 37 030 A1 | 5/1990 |
| DE | 39 37 030 C2 | 5/1990 |
| EP | 3 436 472 | 4/1986 |
| EP | 0 582 361 | 5/1997 |
| EP | 1 147 746 | 10/2001 |
| EP | 1 258 227 | 11/2002 |
| FR | 2 288 495 | 6/1976 |
| GB | 2 191 855 | 12/1987 |
| GB | 2 225 957 | 6/1990 |
| WO | WO 89/12428 | 12/1989 |
| WO | WO 02/053053 | 7/2002 |
| WO | WO 02/058761 | 8/2002 |

OTHER PUBLICATIONS

Premier, drawings and descriptions of *"Peeso Drills"*, *"Pesso Brushes"*, and *"Barbed Broaches"*, p. 29, available on information and belief at least as early as Jan. 23, 2001.

Maag, Ulrich, "Principles of Flocking", pp. 1-6, Reprinted from *Adhesives Age*, Sep. 1975, vol. 18, No. 9.

Borowski, Bob, "Get a Feel for Flocking", pp. 1-4, Reprinted from *Screen Printing*, Mar. 1998.

Advertisement for *Microbrush Disposable Applicators*, believed to be publicly available or known at east as early as Applicants' filing date.

Various Internet Documents for Microbrush Corporation, http://www.microbrush.com; Jan. 9, 2003, 56 pgs.

Microbrush Product, *"Flowthru"*, Available on Information and Belief in 2001, 3 pgs.

* cited by examiner

FIBER-COATED DENTAL INFUSOR SYSTEMS AND METHODS OF USE

BACKGROUND OF THE INVENTION

1. The Field of the Invention

This invention relates to the field of treating bleeding tissues.

2. The Relevant Technology

Dental infuser devices are employed to prevent bleeding on dental tissue, such as the gingiva. Infusor devices typically include a delivery syringe and a tubular cannula extending from the syringe in fluid communication therewith. Upon depressing the syringe plunger, a coagulating medicament is expressed through the cannula and onto the gingiva. The medicament infuses into the tissues, thereby coagulating the blood seeping therefrom.

The tip of the cannula can also be used to scrub the afflicted area, a process commonly known as burnishing. The burnishing action of the cannula tip can force medicament into the tissues and polish and remove excess coagulum from the surface of the tissue and helps to insure that the tissues will not begin to bleed again during the remainder of a dental procedure.

One infusion approach is to apply under hydraulic pressure a coagulant to the gingiva so as to infuse the coagulant into exposed capillaries, and simultaneously rub the gingiva with the medicament in order to remove coagulated blood existing on the surface of the gingiva.

Certain typical devices use air pressure and gravity to force capillary flow through a porous textile for a swabbing effect. However, such devices commonly do not have intricately controlled fluid flow. In addition, swab tipped devices have proved to be too large and wasteful of valuable medicaments and time. Other devices feel foreign to the dentist's trained hand and are awkward to use.

It would be an improvement in the art to eliminate the problems recognized in the art and remedy the dentist's needs by providing a device that is familiar in feel, can easily reach all areas within the mouth or within an incision, provides an intricate burnishing effect, and permits the dentist or doctor to control the flow of medicament.

SUMMARY OF THE INVENTION

A method for controlling bleeding during dental procedures according to the present invention comprises: (i) applying under hydraulic pressure a medicament (e.g., a hemostatic agent, such as a hemostatic coagulant) to a desired area of dental tissue with a delivery system having fibers thereon so as to infuse medicament into exposed capillaries of such tissue such that the blood within the capillaries becomes coagulated; and (ii) rubbing the tissue with the fiber coated medicament delivery system in order to remove coagulated blood existing on the surface of the dental tissue. In one embodiment, the application of the medicament and the rubbing of the tissue are performed simultaneously.

The medicament delivery system that is employed to infuse medicament into dental tissue comprises (i) a medicament delivery device such as a syringe; and (ii) a delivery tip having fibers attached to the distal delivery end of the tip. In use, the syringe is in fluid communication with the delivery tip so as to deliver the medicament to a desired location on the gingiva or other dental tissue. The fibers on a cannula of the delivery tip are employed to furnish the desired burnishing action. The fibers may be attached to the distal delivery end of the delivery tip through electrostatic flocking, for example. The medicament delivery system comprises a hollow body containing a medicament (e.g. within a syringe barrel) in fluid communication with the cannula having a flocked distal delivery end through which the medicament is dispensed under hydraulic pressure.

The syringe type dispenser or other delivery system is configured to deliver a medicament such as a hemostatic coagulating solution to the bleeding tissue. The delivery tip attaches to the syringe and includes a cannula that is preferably (i) rigid and (ii) configured in a desired curved shape to accommodate access to a dental tissue, such as gingival sulci.

The fibers extend from the end of the cannula to thereby provide a rubbing effect without sharpness of the edges of the cannula causing additional bleeding. This effect enables effective burnishing of tissue, aids in removal of coagulated blood, and applies pressure to the tissue.

The medicament is disposed within the syringe or other delivery system. By depressing the plunger of the syringe, the medicament is forced through the delivery tip and exudes onto the point of application. In one embodiment, release of the plunger creates a slight vacuum within the tube, and immediately stops the flow of medicament, thereby preventing further dispensing of medicament.

The medicament delivery system of the present invention can be used in many ways with many different medicaments. By way of example, it can be used to deliver astringent, hemostatic agents to a bleeding gingival sulcus prior to taking impressions, to a bleeding pulp chamber in a pulpotomy, or to a cut papilla interdentally. In addition, however, the medicament delivery system of the present invention can be employed to stop bleeding in a variety of different tissues, such as the facial tissues or other skin portions of a human being. The present invention may be useful to stop bleeding that occurs during shaving, for example.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE ILLUSTRATED EMBODIMENTS

Figure 1:
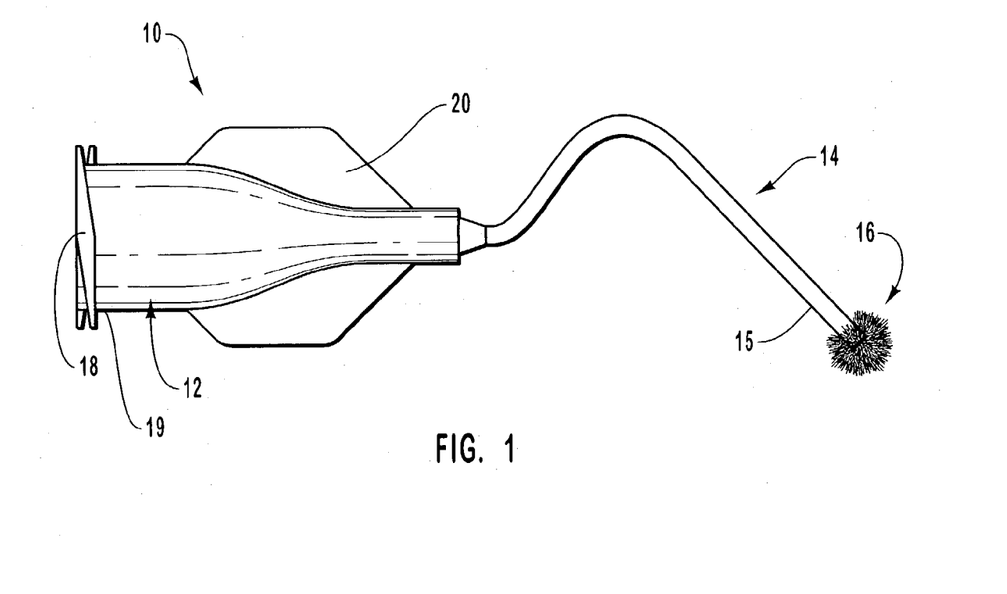
FIG. 1 is a top view of a delivery tip of the medicament delivery system system of the present invention featuring the fiber-coated distal end of the delivery tip.
Figure 2:
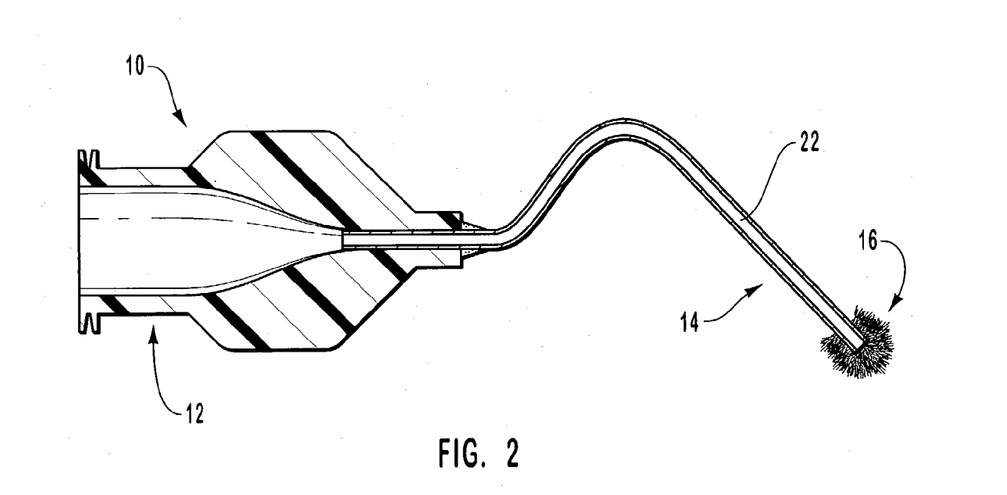
FIG. 2 is a longitudinal section of a the delivery tip of FIG. 1.
Figure 3:
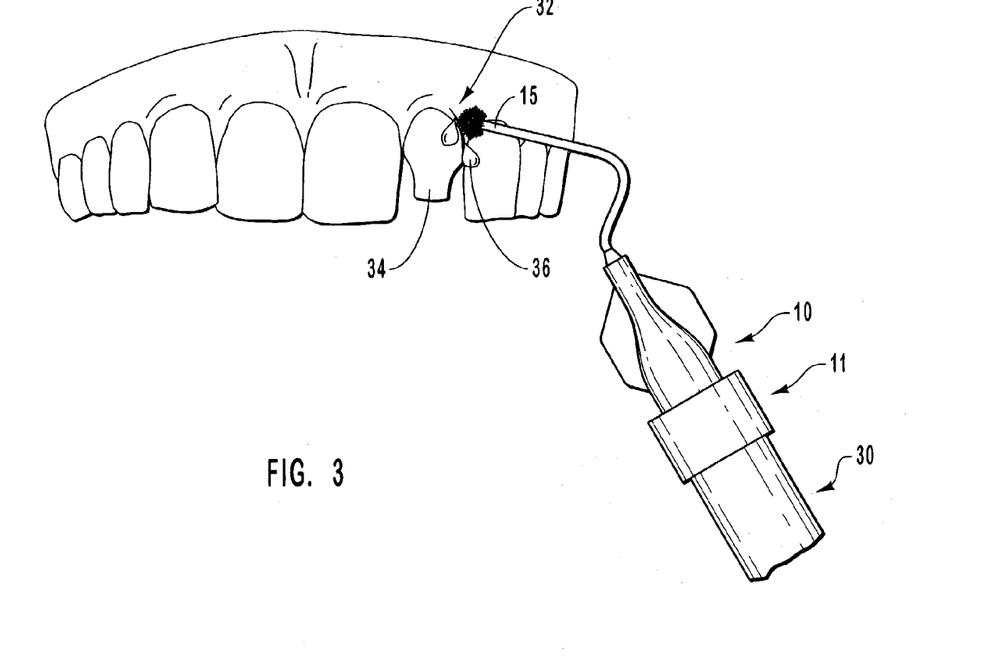
FIG. 3 is a view of a medicament delivery system of the present invention incorporating the delivery tip of FIG. 1 shown with the distal end of the delivery tip placed against bleeding gingival tissue.
Figure 4:
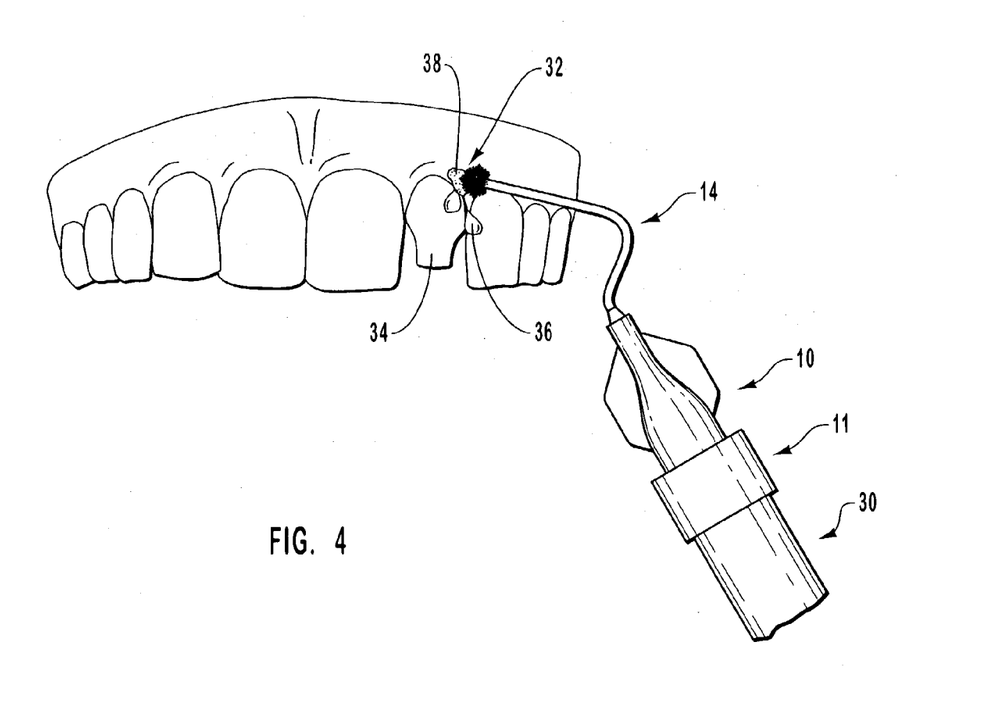
FIG. 4 is a view of the medicament delivery system of FIG. 3 incorporating the delivery tip of FIG. 1 shown applying medicament to bleeding gingival tissue.
Figures 5, 6, 7:
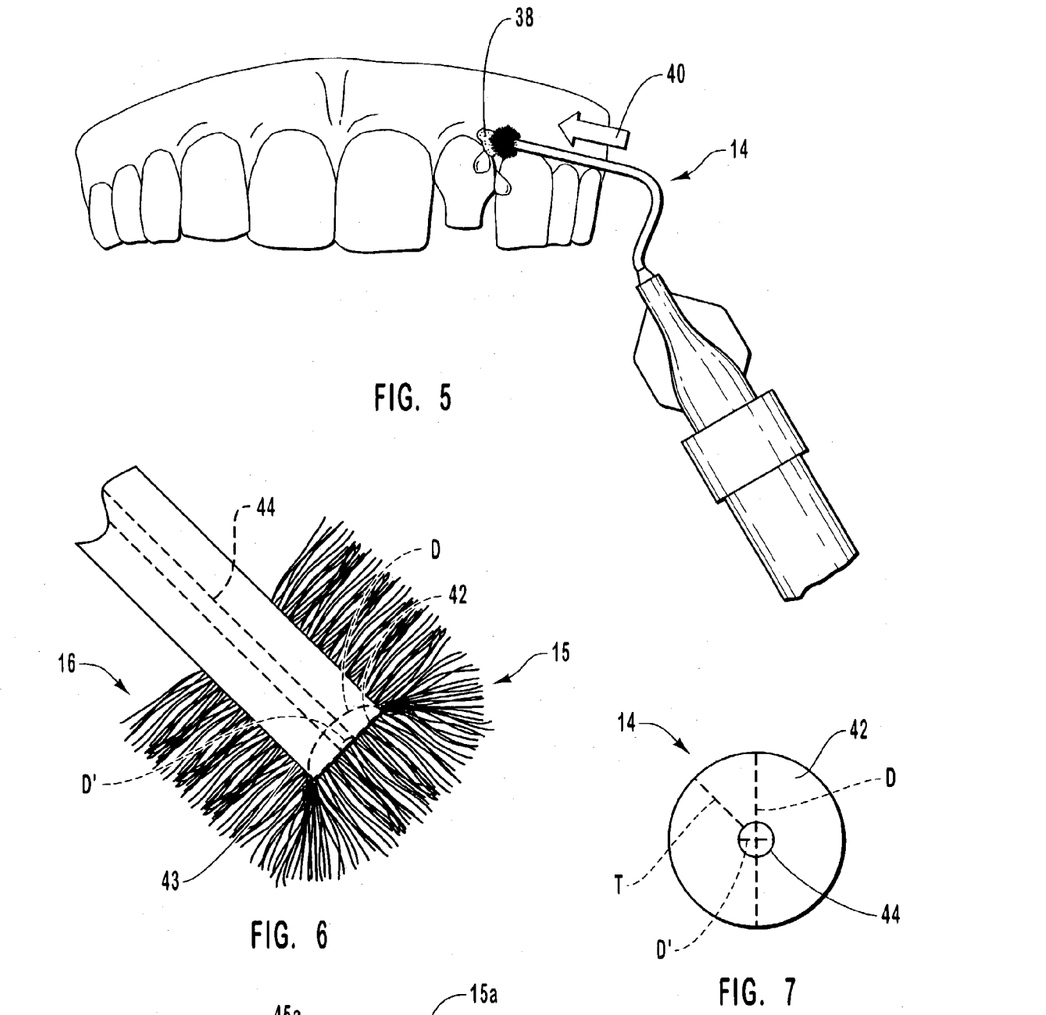
FIG. 5 is a view depicting the burnishment of the dental tissue of FIGS. 3 and 4 with the fiber-coated distal delivery end of the delivery tip of FIG. 1.
FIG. 6 demonstrates an optional delivery tip end of a cannula of the present invention having a thick wall so as to allow deposition of a significant amount of fibers thereon.
FIG. 7 depicts the face of the delivery tip end of the cannula of FIG. 6 having a thick wall on which fibers are deposited.

FIGS. 1 and 2 illustrate an embodiment of a delivery tip 10 of the present invention while FIGS. 3-5 illustrate a method for preventing bleeding that incorporates the delivery system of the present invention. FIGS. 6 and 7 demonstrate an example of a delivery tip end of a cannula of the present invention having a thick wall so as to allow a significant amount of fibers thereon.

As shown in FIGS. 1 and 2, delivery tip 10 has a hollow body 12, an elongate hollow cannula 14 in fluid communication with body 12, and fibers 16 coupled to distal delivery end 15 of hollow cannula 14. Fibers 16 may be the same as or similar to and may be attached in a manner the same as or similar to the fibers discussed in U.S. patent application Ser. No. 10/068,788 filed Feb. 6, 2002 entitled "Fiber-Covered Dental Delivery Instruments," U.S. Pat. No. 6,450,810, entitled "Cushioned, Fiber-Covered Dental Applicators," and/or U.S. Pat. No. 5,816,804 entitled "Fiber-Ended Open Orifice Delivery Tip," each of which is incorporated herein by reference.

Electrostatic flocking is a preferred method for depositing the fibers onto cannula 14 as shown in FIGS. 1 and 2 because the fibers can thereby be deposited in a dense, controlled, uniform manner, and adhere to the surface of the cannula perpendicular to their adhesion sites, such that the resulting mass of fibers provides both an effective burnishing effect, as well as effective cushioning when the distal delivery end 15 is pressed against a dental surface during burnishing. Fibers 16 can be coupled to end 15 through the use of an adhesive, for example.

Body 12 of delivery tip 10 is hollow and has a Luer Lock coupling portion 18 or other threads (or is configured for a friction coupling or the like) at its proximal end 19 such that proximal end 19 is configured to be selectively coupled in fluid communication to a delivery device such as a syringe. As illustrated in FIGS. 1 and 2, the proximal end of elongate hollow cannula 14 is adhered through adhesion or another suitable process to the distal end of body 12 such that cannula 14 is in fluid communication with body 12. As another option, a delivery tip of the present invention is integrally coupled to a delivery device, such as a syringe. As yet another option, a cannula of the present invention is coupled directly to the delivery device, wherein fluid is received within a hollow body of the delivery device.

The cannula of the present invention can be manufactured into a variety of different shapes, such as straight or can be curved to any desired shape to facilitate application of a medicament to difficult to reach areas within the mouth or within an incision or to reach other bleeding areas. Body 12 may be comprised of a rigid plastic material, but may also comprise metal or another material. Cannula 14 is preferably comprised of a metal material so as to retain its rigidity, which is helpful in order to perform burnishing, the rigid cannula being readily pressed against the tissue without buckling and losing control of the burnishing, although a variety of different materials may be employed for cannula 14, such as a rigid plastic. In one embodiment the flow may be restricted in an orifice in the body 12, for example.

Medicament delivery system 11 comprising (i) a delivery device such as a syringe 30 and (ii) delivery tip 10 coupled thereto is shown in FIG. 3. Delivery tip 10 and system 11 comprising (i) tip 10 and (ii) syringe 30 are each examples of an instrument configured for use in a procedure for controlling bleeding. The distal delivery end 15 of tip 10 also represents the distal delivery end of system 11, as shown in FIG. 3.

FIG. 3 illustrates a dental tissue 32 having blood 36 exuding therefrom and a tooth portion 34 that has been prepared to receive a dental impression material thereon preparatory to have a crown placed thereon. As shown in FIG. 3, the distal delivery tip 15 of system is placed against tissues 32 preparatory to the medicament contained within syringe 30 being deposited onto tissues 32. Syringe 30 has a hollow body (e.g., the barrel of the syringe) containing the medicament to be delivered and a plunger configured such that movement of the plunger causes the medicament to flow under pressure through delivery tip 10 onto a desired area.

FIG. 4 illustrates the delivery of medicament 38 onto the bleeding dental tissue 32. This may be performed, for example, in order to prevent blood 32 from seeping onto tooth 34 prior to making an impression thereof. During delivery of medicament 38 from syringe 30 through cannula 14, the medicament is pressed through the fibers 16 on the face 42 (FIGS. 6–7) of the distal delivery end 15 of cannula 14. The medicament 38 is infused through dental tissues 32 (e.g., gingiva) through the hydraulic pressure exerted during delivery and/or during the burnishing action illustrated in FIG. 5. As illustrated in FIG. 5, moving fibers 16 force medicament 38 into the dental tissues 32, as illustrated by the arrow 40 representing movement of delivery tip 14 against the dental surface 23

The burnishing action enabled by the fibers 16 may occur simultaneously with the delivery of the medicament 38 or may occur following the delivery of the medicament 38. In one embodiment, fibers 16 are so densely oriented on the distal delivery end 15 as to provide some back pressure against the positive pressure of the plunger or other device used to deliver the medicament so as to help regulate the flow of medicament.

Thus, system 11 thus contains a medicament (namely in syringe 30) and has a cannula 14 in fluid communication therewith having a fiber coated distal delivery end 15 through which the medicament is dispensed under hydraulic pressure. Consequently, a method for controlling bleeding using medicament delivery system 11 comprises: (i) applying under hydraulic pressure a medicament to a desired area of dental tissue 32 using the delivery system 11 so as to infuse medicament into exposed capillaries of such tissue 32 such that the blood within said capillaries becomes coagulated, as shown in FIG. 4; and (ii) rubbing the tissue 32 with said medicament delivery system in order to remove coagulated blood existing on the surface of the dental tissue as shown in FIG. 5 so as to substantially prevent reinitiation of bleeding. The act of rubbing the tissue 32 with the medicament delivery system may be performed simultaneously with the act of applying the coagulant under hydraulic pressure.

In a further embodiment of the present invention, the method for controlling bleeding includes providing sealing engagement of the distal delivery end 15 of the delivery system 11 with the dental tissue 32 as illustrated in FIGS. 3 and 4 sufficient to cause some back pressure against the medicament under pressure in the cannula, thereby regulating the infusion of the medicament into the exposed capillaries of the gingival tissue. Delivery system 11 is thus capable of controlled dispensing of a medicament under pressure.

A further embodiment of the present invention comprises (i) providing a delivery system capable of controlled dispensing of a medicament under pressure, such as system 11; (ii) placing the delivery system against gingival tissue 32 in order to provide sealing engagement of the fiber coated delivery end 15 of the delivery system 11 with the gingival tissue 32 sufficient to cause some back pressure against the pressure of the medicament being dispensing by the delivery system 11, as illustrated in FIG. 3, thereby regulating the flow of the medicament through the delivery system 11; (iii) infusing the medicament into the gingival tissue under pressure, as illustrated in FIG. 4; and (iv) mechanically burnishing the surface of the gingival tissue 32 by moving the fiber coated delivery end 15 while delivery end 15 is in contact with the gingival tissue 32, as illustrated in FIG. 5, thus removing coagulum from the surface of the gingival tissue 32.

In a further embodiment of the present invention, a method for infusing controlled amounts of a hemostatic agent to bleeding gingival tissue 32 of a patient during a dental procedure comprises: (i) providing a delivery system 11 capable of controlled dispensing of a hemostatic agent by hydraulic pressure through a fiber coated delivery end 15 of the system 11; (ii) placing the fiber coated end 15 of the system 11 against the bleeding gingival tissue 32 of the patient, as shown in FIG. 3; (iii) infusing under pressure the hemostatic agent into the openings of the capillaries of the bleeding gingival tissue 32, as shown in FIG. 4 such that hemostasis occurs in the ends of the capillaries; and (iv) burnishing the gingival tissue 32 with the fiber coated end 15 as shown in FIG. 5 so as to remove coagulated blood on the surface of the gingival tissue 32.

Burnishing the tissue 32 may be performed while providing sealing engagement of the fiber coated end 15 with the tissue 32 of the patient sufficient to cause some back pressure against the hydraulic pressure provided by system 11. In one embodiment, the tissue is simultaneously burnished with the fiber-coated end 15 while the hemostatic agent is infused into the tissue by hydraulic pressure.

Cannulas 14 of varying size may be employed in the present invention However, in one embodiment, the cannula 14 is larger than typical delivery tip cannulas 14 in order to increase the rigidity of the cannula 14 and in one embodiment, in order to increase the surface area of the face of the distal delivery end 15. Nevertheless, it is desirable to have a cannula that can fit between teeth or between a tooth and a tooth remnant tooth portion (e.g., tooth portion 34) that has been prepared to receive an impression material thereon. For example, in one embodiment, the gauge of the cannula 14 is in the range of about 13 gauge to about 25 gauge, preferably about 18 to about 22 gauge, more preferably about 19 gauge to about 21 gauge. In one embodiment, cannula 14 has a gauge size of larger than 23 gauge in order to provide sufficient strength to press cannula 14 against dental tissue 32 and remain sufficiently rigid.

With reference now to FIGS. 6 and 7, increasing the thickness "T" of the wall of a cannula 14 increases the surface area available for fibers 16, thereby increasing the amount of fibers 16 that can be placed on the face 42 of distal delivery end 15 of cannula 14. On the other hand, it is simultaneously desired to provide a cannula 14 that can fit into small spaces, such as a gingival sulcus, and to provide a cannula 14 that can receive a sufficiently viscous medicament through a passageway 44 thereof that can stop bleeding. Thus, the outer diameter D, inner diameter D' and wall thickness "T" are synchronized in order to achieve the best overall results.

In addition, in one embodiment, a relatively thick layer of an adhesive material may be placed onto the cannula, such as to provide an adhesive and/or cushioning effect, as discussed in U.S. Pat. No. 6,450,810, which is incorporated herein by reference. This dynamic may affect the size of the cannula that is selected.

Keeping those factors in mind, in order to achieve the best results, in one embodiment, the thickness "T" of the wall of cannula 14 is more than 0.007 inch, preferably more than about 0.008 inch, more preferably more than about 0.010 inch, such as more than 0.012 inch. By increasing the thickness "T" of the wall, and thus the amount of fibers 16 on the wall, the chances of cutting the patient are reduced and more fibers 16 are available for burnishing.

In one embodiment, the outer diameter "D" of cannula 14 is in the range of about 0.028 inch to about 0.05 inch (e.g., 0.036 inch) and the inner diameter "D'" cannula 14 is in the range of about 0.006 inch to about 0.012 inch, (e.g., 0.008 inch). For example, in one embodiment the inner diameter "D'" of cannula 14 is about 0.008 inch while the outer diameter "D" of cannula 14 is about 0.036 inch. In one embodiment, the thickness "T" of the wall of cannula 14 is in the range of about 0.008 inch to about 0.022 inch.

Examples of possible outer diameters, inner diameters, and wall thicknesses of various gauges of cannulas of the present invention are shown in Tables 1 and 2 below:

TABLE 1

| Gauge | Outer Diameter (inch) | Inner Diameter (inch) | Wall Thickness (inch) |
|---|---|---|---|
| 18 | 0.0500 | 0.0060 | 0.0220 |
| 19 | 0.0420 | 0.0060 | 0.0180 |
| 20 | 0.0360 | 0.0060 | 0.0150 |
| 21 | 0.0320 | 0.0060 | 0.0130 |
| 22 | 0.0280 | 0.0060 | 0.0110 |

TABLE 2

| Gauge | Outer Diameter (inch) | Inner Diameter (inch) | Wall Thickness (inch) |
|---|---|---|---|
| 18 | 0.0500 | 0.0120 | 0.0190 |
| 19 | 0.0420 | 0.0120 | 0.0150 |
| 20 | 0.0360 | 0.0120 | 0.0120 |
| 21 | 0.0320 | 0.0120 | 0.0100 |
| 22 | 0.0280 | 0.0120 | 0.0080 |

Such embodiments of cannulas having thick walls are designed to hold a variety of different fibers 16 on the face 42 of the cannula 14 such that the density of the fibers 16 located on the face 42 of the cannula 14 is sufficient to provide cushioning against the tissue of the user. The additional fibers 16 made available by increasing the size of the face 42 thus decrease the chance of cutting the patient's gums and provide better density for scrubbing. In addition, the small hole acts as a flow restrictor.

The fiber lengths and diameters of fibers 16 may vary according to the needs of a particular user. The fiber lengths are desirably sufficiently rigid in order to provide a desired brushing action, yet are soft enough not to cause the tissues to bleed. Examples of fiber lengths for the fibers 16 include lengths of to about 0.3 mm to about 3 mm, preferable about 0.5 mm to about 2 mm, more preferably about 1 mm to about 2 mm, e.g., about 1.5 mm. For example, in one embodiment, fiber thicknesses in the range of about 1 denier to about 100 denier, e.g., preferably about 1.5 denier to about 30 denier (such as about 3 denier to about 15 denier) may be employed. In one embodiment the fibers 16 have a length of about 1.5 mm and have a thickness of about 6 denier.

As another example of a delivery device of the present invention, another embodiment of the present invention utilizes a unit dose syringe that is preloaded or a disposable squeeze bulb and has a cannula, such as cannula 14 in fluid communication therewith. With this alternative embodiment, the flow of medicament may be controlled by squeeze pressure between the thumb and fingers.

Other examples of delivery devices that may be employed in the present invention are featured in (i) U.S. Pat. No. 6,450,810, entitled "Cushioned, Fiber-Covered Dental Applicators;" and (ii) U.S. Pat. No. 4,941,873, entitled Controlled Diffusion Medicament delivery system, which are incorporated herein by reference.

The use of electrostatic flocking to couple fibers 16 to cannula 12 has a variety of different advantages. First, fibers 16 can be applied in a dense, uniform manner. Consequently, fibers 16 are substantially parallel to each other. The dense, parallel nature of the fibers 16 enhances the formation of air pockets between fibers 16. The fibers 16 are not matted down on top of each other. The formation of air pockets between adjacent fibers 16 promotes the receipt of medicament therein during burnishing. By electrostatically applying fibers 16 of different lengths, the texture can be conveniently varied. Furthermore, the longer fibers are supported by shorter fibers, preventing the matting of the fibers. The use of fibers 16 of varying length can also assist in the formation of air pockets for the entrapment of medicament therein.

Figure 8:
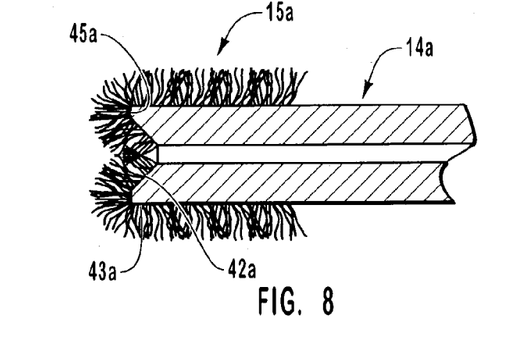
FIG. 8 depicts an alternative distal delivery end of a cannula having a conical shaped inner diameter surface such that fluid moves out more quickly to the fibers and tissues.

FIG. 8 depicts an alternative distal delivery end 15a of a cannula 14a having a conical shaped face 42a such that fluid moves out more quickly to the fibers 16a and bleeding tissues. The fibers may be mounted on the face 42a, the outside 43a, and/or on flat rim portions 45a only, or on sides 43a, face 42a, and flat rim portion 45a as shown. The conical face 42a can have a variety of different angles. Optionally, the outside 43 (and/or inside) portion of the wall of the cannula can be tapered.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for controlling bleeding using a medicament delivery system having a fiber coated distal delivery end, the fiber coated distal delivery end having densely oriented fibers so as to partially obstruct the distal delivery end and provide back pressure against pressurized medicament within the distal delivery end of the delivery system so as to assist in regulating medicament flow, the method comprising:

applying a medicament to a desired area of tissue using the delivery system so as to infuse medicament into exposed capillaries of such tissue such that the blood within said capillaries becomes coagulated, the densely oriented fibers providing back pressure against pressured medicament within the distal delivery end of the delivery system; and rubbing the tissue with the fiber coated delivery end of said medicament delivery system in order to remove coagulated blood existing on the surface of the tissue.

2. The method as recited in claim 1 wherein the tissue is rubbed with the fiber coated end of the delivery system while the medicament is being applied under hydraulic pressure to a desired area.

3. A method as recited in claim 1 wherein the thickness of a wall of a cannula of the delivery system is greater than 0.007 inch.

4. The method as recited in claim 1 wherein the thickness of a wall of a cannula of the delivery system is greater than about 0.008 inch.

5. A method for controlling bleeding using a medicament delivery system as defined in claim 1, further comprising providing sealing engagement of the distal delivery end of the delivery system with the dental tissue sufficient to cause additional back pressure against the medicament under pressure in the cannula, thereby further regulating the infusion of the medicament into the exposed capillaries.

6. A method for controlling bleeding using a medicament delivery system, said medicament delivery system containing a medicament and having a cannula having a fiber coated distal delivery end and a passageway through which the medicament is dispensed under hydraulic pressure, the cannula having a cylindrical cross section, the cannula having a wall thickness that is greater than an inner diameter of the passageway so as to provide increased surface area to which fibers are attached to increase cushioning against tissue during use, the method comprising:

applying under hydraulic pressure a medicament to a desired area of tissue using the delivery system so as to infuse medicament into exposed capillaries of such tissue such that the blood within said capillaries becomes coagulated; and rubbing the tissue with the fiber coated delivery end of said medicament delivery system in order to remove coagulated blood existing on the surface of the tissue, the fibers providing cushioning so as to protect the tissue from cutting by the cannula while rubbing the tissue.

7. A method for controlling bleeding as recited in claim 6, wherein applying the medicament and rubbing the tissue are performed simultaneously.

8. The method as recited in claim 6 wherein the density of the fibers located on the cannula is such that there is sufficient cushioning against the tissue of the user.

9. The method as recited in claim 6 wherein the fibers are uniformly coupled to the distal delivery end of the cannula.

10. The method as recited in claim 6 where in the delivery system is configured such that the medicament is forced through the fibers before contacting the tissue of the patient.

11. The method as recited in claim 6 wherein the thickness of wall of the cannula is greater than about 0.010 inch.

12. The method as recited in claim 6, wherein the thickness of a wall of the cannula is greater than about 0.012 inch.

13. A method as recited in claim 6, wherein the fibers are coupled to the cannula through electrostatic flocking.

14. A method for infusing controlled amounts of a medicament into gingival tissue of a patient during a dental procedure, comprising:
   (i) providing a delivery system capable of controlled dispensing of a medicament under pressure, the delivery system having a fiber coated distal delivery end in which fibers are attached to both a distal face and an adjacent outer sidewall of the distal delivery end in order to provide a cushion so as to protect tissue from an otherwise sharp edge at an intersection of the distal face and adjacent outer sidewall;
   (ii), placing the delivery system against gingival tissue in order to provide sealing engagement of the fiber coated delivery end of the delivery system with the gingival tissue sufficient to cause some back pressure against the pressure of the medicament being dispensing by the delivery system, thereby regulating the flow of the medicament through the delivery system;
   (iii) infusing the medicament into the gingival tissue under pressure; and
   (iv) mechanically burnishing the surface of the gingival tissue by moving the fiber coated delivery end while delivery end is in contact with the gingival tissue, thus removing coagulum from the surface of the gingival tissue,
   the fibers attached to the distal face and adjacent outer sidewall protecting the gingival tissue from the otherwise sharp edge while providing sealing engagement of the delivery end with the gingival tissue sufficient to cause back pressure and also while mechanically burnishing the gingival tissue.

15. A method as recited in claim 14, wherein the fibers are coupled to the cannula through electrostatic flocking.

16. The method as recited in claim 14, wherein the fibers are uniformly coupled to the distal delivery end of the cannula.

17. A method for infusing controlled amounts of a hemostatic agent to tissue of a patient during dental procedures, the method comprising:
   (i) providing a delivery system capable of controlled dispensing of a hemostatic agent by hydraulic pressure through a fiber coated delivery end of the delivery system, the fiber coated delivery end having a conical surface to which fibers are attached;
   (ii) placing the fiber coated end of the delivery system against the tissue of the patient;
   (iii) infusing under pressure the hemostatic agent into the openings of the capillaries of the tissue such that hemostasis occurs in the ends of the capillaries; and
   (iv) burnishing the tissue with the fiber coated end so as to remove coagulated blood on the surface of the tissue.

18. A method as defined in claim 17, wherein the burnishing of the tissue further comprises providing sealing engagement of the fiber coated end of the delivery system with the tissue of the patient sufficient to cause some back pressure against the hydraulic pressure provided by the delivery system.

19. A method as defined in claim 17, wherein the tissue is simultaneously burnished with the fiber coated end of the delivery system while the hemostatic agent is infused into the tissue by hydraulic pressure.

20. An instrument configured for use in a procedure for controlling bleeding, the instrument comprising:
   a hollow body configured to receive medicament therein; and
   a rigid cannula having a proximal end and a distal delivery end, the proximal end of the cannula being coupled to the hollow body in fluid communication with the hollow body, the cannula having a cylindrical cross section defined by a wall having a passageway therethrough, wherein the wall has a thickness of greater than 0.007 inch, the wall thickness exceeding an internal diameter of the passageway; and
   a plurality of fibers coupled to the distal delivery end of the cannula, such that medicament is expressable though the cannula onto bleeding tissue and such that the distal delivery end is configured for rubbing the tissue with the fiber coated delivery end in order to remove coagulated blood existing on the surface of the tissue.

21. An instrument as recited in claim 20, wherein the instrument is a delivery system.

22. An instrument as recited in claim 21, wherein the delivery system comprises a delivery tip and a syringe.

23. An instrument as recited in claim 20, wherein the instrument is a delivery tip.

24. An instrument as recited in claim 20, wherein the cannula comprises plastic.

25. An instrument as recited in claim 20, wherein the fibers are coupled to the cannula though electrostatic flocking.

26. An instrument as recited in claim 20, wherein the thickness of the cannula wall is greater than about 0.01 inch.

27. An instrument as recited in claim 20, wherein the face of the cannula has a conical surface.

28. An instrument as recited in claim 27, wherein a plurality of fibers are located on the conical surface of the cannula.

29. A dental delivery tip configured for use in a procedure for controlling bleeding, the dental delivery tip comprising:
   a hollow body configured to receive medicament therein; and
   a rigid cannula having a proximal end and a distal delivery end, the proximal end of the cannula being coupled to the hollow body in fluid communication with the hollow body, the cannula having a wall having a passageway therethrough, wherein the wall has a thickness of greater than 0.007 inch; and
   a plurality of fibers coupled to the distal delivery end of the cannula and being densely oriented so as to partially obstruct the distal delivery end and provide back pressure against pressurized medicament within the distal delivery end of the delivery system so as to assist in regulating flow of, medicament through the cannula onto bleeding tissue so as to infuse medicament into exposed capillaries of such tissue such that the blood within said capillaries can become coagulated and such that the distal delivery end is configured for rubbing the tissue with the fiber coated delivery end in order to remove coagulated blood existing on the surface of the tissue.

30. A dental instrument as recited in claim 29, wherein the fibers are coupled to the cannula through electrostatic flocking.

31. A dental instrument as recited in claim 29, wherein the face of the cannula has a conical surface and wherein a plurality of fibers are located on the conical surface of the cannula.

32. A dental instrument as recited in claim 29, wherein the delivery tip is configured to be coupled to a delivery device.

33. An instrument as recited in claim 29, wherein the density of the fibers located on the cannula is such that there is sufficient cushioning against the tissue of the user.

34. The instrument as recited in claim 29 wherein the fibers are uniformly coupled to the distal delivery end of the cannula.

35. The instrument as recited in claim 29 where in the tip is configured such that the medicament is forced through the fibers before contacting the tissue of the patient.

36. A dental medicament delivery system configured for controlling bleeding, the dental instrument comprising:
  a delivery device; and
  a delivery tip, the delivery tip configured to be in fluid communication with the delivery device, the delivery tip comprising:
  a hollow body configured to receive medicament therein; and
  a rigid cannula having a proximal end and a distal delivery end having a conical surface, the proximal end of the cannula being coupled to the hollow body in fluid communication with the hollow body, the cannula having a wall having a passageway therethrough, wherein the wall has a thickness of greater than 0.007 inch; and
  a plurality of fibers coupled to the distal delivery end of the cannula, including the conical surface, such that medicament is expressable through the cannula onto bleeding tissue so as to infuse medicament into exposed capillaries of such tissue such that the blood within said capillaries becomes coagulated and such that the distal delivery end is configured for rubbing the tissue with the fiber coated delivery end in order to remove coagulated blood existing on the surface of the tissue so as to substantially prevent reinitiation of bleeding.

37. A system as recited in claim 36, wherein the delivery tip is configured to be selectively coupled to the delivery device.

38. An instrument configured for use in a procedure for controlling bleeding, the instrument comprising:
  a hollow body configured to receive medicament therein; and
  a cannula having a proximal end and a distal delivery end, the proximal end of the cannula being coupled to the hollow body in fluid communication with the hollow body, the cannula having a cylindrical cross section defined by a wall having a passageway therethrough, wherein the inner diameter of the cannula is in the range of about 0.006 inch to about 0.012 inch, wherein the wall has a thickness that exceeds the inner diameter of the cannula; and
  a plurality of fibers coupled to the distal delivery end of the cannula, such that medicament is expressable through the cannula onto bleeding tissue and such that the distal delivery end is configured for rubbing the tissue with the fiber coated delivery end in order to remove coagulated blood existing on the surface of the tissue.

39. An instrument as recited in claim 38, wherein the cannula has an outer diameter in the range of about 0.028 inch to about 0.05 inch.

40. An instrument as recited in claim 38, wherein the fibers have a length of about 0.3 mm to about 3 mm.

41. An instrument as recited in claim 38, wherein the thickness of the wall of the cannula is in the range of about 0.008 inch to about 0.020 inch.

* * * * *

UNITED STATES PATENT AND TRADEMARK OFFICE
CERTIFICATE OF CORRECTION

PATENT NO. : 7,198,623 B2  Page 1 of 1
APPLICATION NO. : 10/340198
DATED : April 3, 2007
INVENTOR(S) : Fischer et al.

It is certified that error appears in the above-identified patent and that said Letters Patent is hereby corrected as shown below:

Column 2
Line 56, after "delivery system" delete "system"
Line 58, after "section of" delete "a"

Column 4
Line 39, after "23" insert --.--
Line 48, after "system 11" delete "thus"

Column 5
Line 49, after "invention" insert --.--

Column 6
Line 63, after "tissue" insert --32--

Column 8
Line 63, claim 11 before "wall" insert --a--

Column 10
Line 48, claim 29 after "flow of" delete ","

Column 12
Line 32, claim 41 change "0.020" to --0.022--

Signed and Sealed this

Twentieth Day of November, 2007

JON W. DUDAS
*Director of the United States Patent and Trademark Office*